United States Patent
Austin

(10) Patent No.: US 7,351,981 B2
(45) Date of Patent: Apr. 1, 2008

(54) METHOD AND APPARATUS FOR MEASURING PURITY OF NOBLE GASES

(75) Inventor: Robert Austin, Largo, FL (US)

(73) Assignee: Constellation Technology Corporation, Largo, FL (US)

( * ) Notice: Subject to any disclaimer, the term of this patent is extended or adjusted under 35 U.S.C. 154(b) by 269 days.

(21) Appl. No.: 11/350,240

(22) Filed: Feb. 8, 2006

(65) Prior Publication Data

US 2007/0181818 A1 Aug. 9, 2007

(51) Int. Cl.
  *G01J 1/42* (2006.01)
(52) U.S. Cl. .................. 250/373; 250/372; 324/484
(58) Field of Classification Search ............. 250/372, 250/373; 324/464
  See application file for complete search history.

(56) References Cited

U.S. PATENT DOCUMENTS 5,747,118 A * 5/1998 Bunshah et al. ........... 427/577
7,309,992 B2 * 12/2007 Kudryavtsev et al. ...... 324/464
2003/0089850 A1 * 5/2003 Putvinski et al. ........... 250/291
2004/0056206 A1 * 3/2004 Bolozdynya et al. ..... 250/385.1

* cited by examiner

*Primary Examiner*—David Porta
*Assistant Examiner*—Djura Malevic
(74) *Attorney, Agent, or Firm*—Larson & Larson; Frank Liebenow

(57) ABSTRACT

A device for detecting impurities in a noble gas includes a detection chamber and a source of pulsed ultraviolet light. The pulse of the ultraviolet light is transferred into the detection chamber and onto a photocathode, thereby emitting a cloud of free electrons into the noble gas within the detection chamber. The cloud of electrons is attracted to the opposite end of the detection chamber by a high positive voltage potential at that end and focused onto a sensing anode. If there are impurities in the noble gas, some or all of the electrons within the cloud will bond with the impurity molecules and not reach the sensing anode. Therefore, measuring a lower signal at the sensing anode indicates a higher level of impurities while sensing a higher signal indicates fewer impurities. Impurities in the range of one part per billion can be measured by this device.

37 Claims, 6 Drawing Sheets

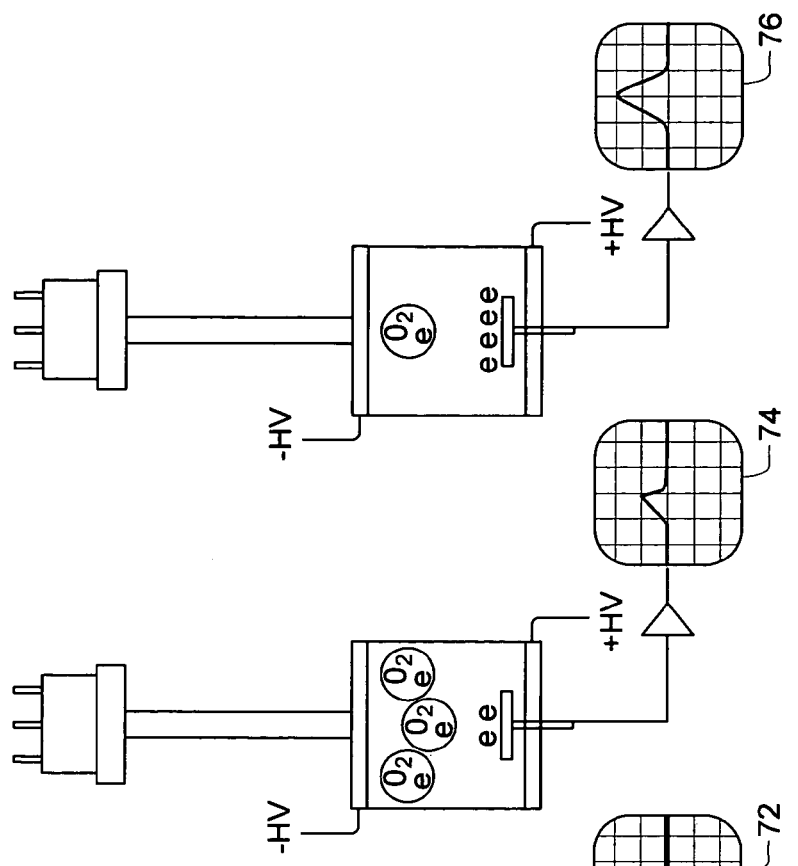
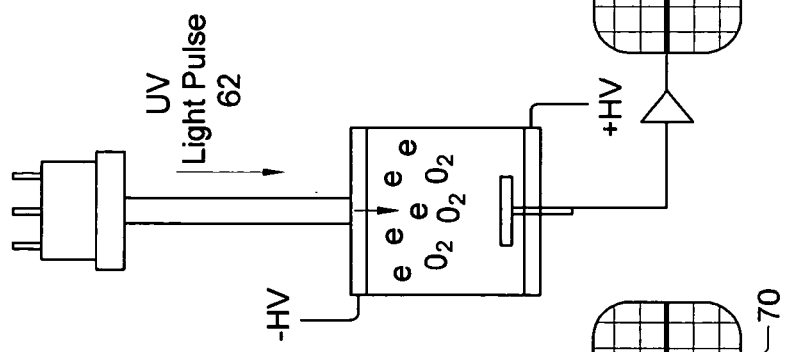
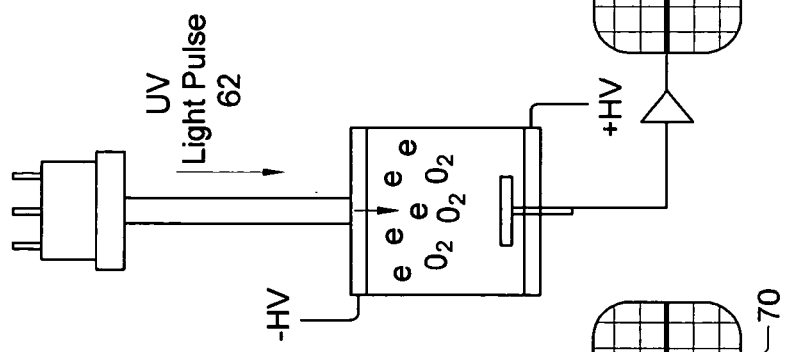
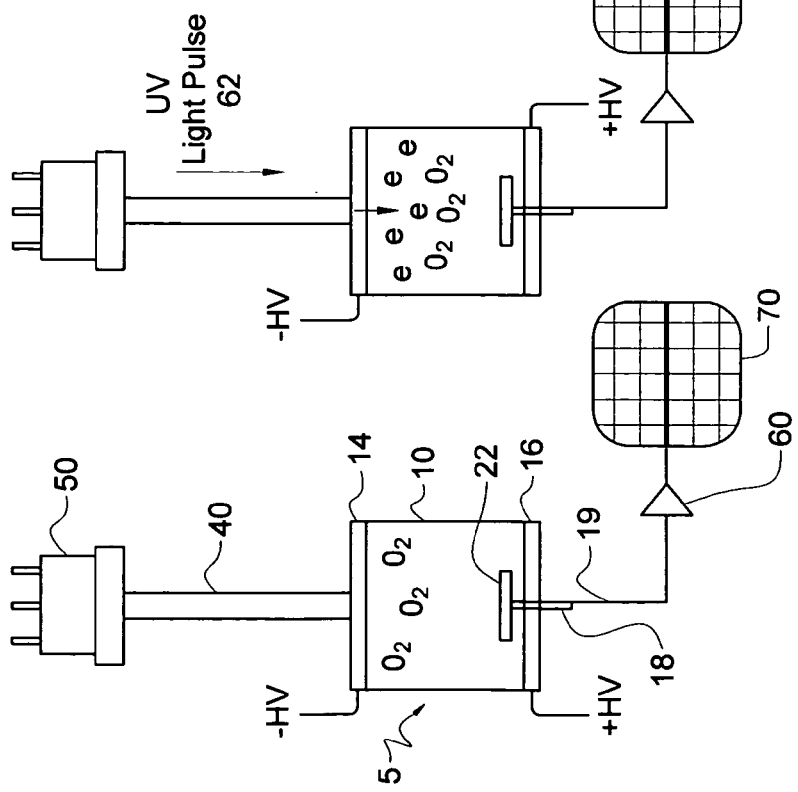

METHOD AND APPARATUS FOR MEASURING PURITY OF NOBLE GASES

This invention was made with U.S. Government support under contract or grant DE-FG02-04-ER83927 awarded by the Department of Energy. The U.S. Government has certain rights in the invention.

BACKGROUND OF THE INVENTION

1. Field of the Invention

This invention relates to the field of measuring impurities in gases and more particularly to a system for measuring impurity levels in noble gases.

2. Description of the Related Art

Noble gases are used in many applications. One example of a noble gas is Xenon, an odorless, colorless, tasteless, nontoxic, monatomic and chemically inert gas. Very small percentages of Xenon gas are normally present in the atmosphere, approximately one part in ten million of dry air. Xenon gas (Xe) is principally shipped and used in liquid or gaseous form and is used in various applications including radiation detection, lasers, ion propulsion, light bulbs, window insulation, medical applications and laboratory research. Xenon gas manufacturers such as, Spectra Gases, Inc., sell standard grades of Xenon gas that are on the order of 99.995% to 99.999% pure, having, for example, from 0.05 parts per million (ppm) up to 1.0 ppm of Oxygen ($O_2$), although slightly higher purity levels are also available.

Another example of a noble gas is Argon (Ar) which is present in the air at a rate of about 1 percent. Argon is readily available in purity levels of up to 99.9995% (research grade), which is fine for welding, plasma jet torches and filling light bulbs. Argon is also used in the production of impurity-free silicon crystals used in the production of semiconductors. As the requirement for larger silicon crystals increases, e.g., for larger integrated circuit die sizes, the demand for higher purity levels increases.

For use in some applications such as certain radiation detectors, gas purity of around one part per billion (ppb) is needed. Among the noble gases, Xenon (Xe) is considered the most difficult to purify, which is unfortunate because it is the most widely used. In many uses of Xenon (Xe), the most damaging contaminants are so-called electro-negative molecules such as oxygen ($O_2$), water ($H_2O$), nitrous oxide ($N_2O$) and carbon monoxide (CO). These molecules inhibit the operation of very sensitive detectors because they trap electrons.

There are known ways to remove impurities such as Oxygen ($O_2$) from a noble gas such as Xenon (Xe). One method of purifying Xenon (Xe) of electro-negative molecules is to initiate a spark between a titanium electrode and a stainless steel electrode that are immersed in the liquid Xenon (Xe). The spark creates titanium dust that readily oxidizes by mixing with any available electro-negative molecules. Methods such as this are known to iteratively produce Xenon (Xe) gas with electro-negative purity levels at or below one part per billion (<1 ppb), but it is very difficult to know when the desired electro-negative purity level is achieved.

Although there are known methods to purify noble gases, it is very difficult to measure the impurities in the noble gas at concentrations of less than one part per million (<1 ppm). One method to measure the electro-negative contamination of liquid Xenon gas is to use the charge deposited by cosmic ray muons. In this, a tank is filled with the Xenon (Xe) liquid under high pressure. Within the tank is an electron drift region formed by a stacked series of rings insulated from one another by ceramic insulators. A negative high voltage is divided by a resistor network, and each tap is applied in order to the conductive rings. Within the tank is a stainless steel anode that is connected to a high-gain amplifier. In our atmosphere, we are constantly bombarded with cosmic ray particles. As each cosmic ray particle hits the Earth's atmosphere, a nuclear reaction occurs which produces pions that decay into muons. When a muon passes through the Xenon gas, it produces an ionized path of electrons and ions. The electrons are drawn by the electric field toward the anode, inducing a signal that is amplified by the high-gain amplifier and, thereby, detected. If the Xenon (Xe) gas was 100% pure, all of the liberated electrons would reach the anode and be detected. The presence of electronegative impurities reduces the number of electrons reaching the anode and, thereby, the amplitude of the induced signal. The average magnitude of the detected signal is measured to determine the estimated purity of the Xenon (Xe). Unfortunately, to achieve a useful measurement, many muons must pass through the Xenon (Xe) gas. Since the rate of interaction of muons within the Xenon (Xe) chamber is typically of the order of one per minute, approximately one half of an hour of measurements is required to make a reliable measurement.

What is needed is a method and apparatus that will quickly and accurately measure the purity of a noble gas.

SUMMARY OF THE INVENTION

An objective of the present invention is to accurately and quickly measure impurities within a noble gas.

Another-objective of the-present invention is to accurately and quickly measure impurities within a noble gas without the use of a laser.

In one embodiment, a device for detecting impurities within a noble gas is disclosed including an impurity detection chamber for holding the noble gas in liquid form that includes a hollow body; a conductive cathode affixed to one end of the hollow body; a conductive ground plate affixed to a distal end of the hollow body; and a conductive sensing anode within the impurity detection chamber near to and insulated from the conductive ground plate and connected to a conductive sensing lead which is insulated from and passes through the conductive ground plate. A pulsed ultraviolet light source is connected to a first end of a light-transmitting pipe which passes through the conductive cathode, and into the impurity detection chamber. The light-transmitting pipe transmits ultraviolet light from the pulsed ultraviolet light source into the impurity detection chamber and onto a photocathode that is painted or plated upon a second end of the light-transmitting pipe. It is preferred that the photocathode be in electrical contact with the conductive cathode.

In another embodiment, a method for detecting impurities within a noble gas is disclosed including providing an impurity detection chamber for holding the noble gas in liquid form. The impurity detection chamber includes a hollow body; a conductive cathode affixed to one end of the hollow body, the conductive cathode connected to a negative source of electricity; a conductive ground plate affixed to a distal end of the hollow body, the conductive ground plate connected to a ground potential; and a conductive sensing anode within the impurity detection chamber near to and insulated from the conductive ground plate and connected to a conductive sensing lead which is insulated from and passes through the conductive ground plate. Next, the impurity detection chamber is filled with the noble gas in liquid form.

To perform a measurement, a pulse of ultraviolet light is emitted from a source of pulsed ultraviolet light and conducted into the impurity detection chamber and onto a photocathode, thereby creating a cloud of electrons. It is preferred that the photocathode be in electrical contact with the conductive cathode.

The cloud of electrons drifts towards the conductive sensing anode by way of the voltage potential at the conductive ground plate being more positive with respect to the conductive cathode. The voltage potential created by a number of electrons from the cloud of electrons that reach the sensing anode is measured, whereby the number of electrons reaching the sensing anode varies with the amount of impurities within the noble gas.

In another embodiment, a device for detecting impurities within a noble gas is disclosed including an impurity detection chamber for containing the noble gas in liquid form, the impurity detection chamber includes a hollow body including a stack of discrete conductive elements that are insulated from each other by spacers, thereby forming a drift field in the chamber; a conductive cathode is affixed one end of the body; a conductive ground plate is affixed to a distal end of the body; a high voltage source of direct current whereby the most negative potential of the direct current is applied to the conductive cathode and the conductive ground plate is at ground potential and the high voltage source is divided into substantially equal potentials, each of the equal potentials connected, in order, to the conductive elements. A conductive sensing anode is situated within the impurity detection chamber near to and insulated from the conductive ground plate, the conductive sensing anode connected to a conductive sensing lead which is insulated from and passes through the conductive ground plate. The device has a pulsed ultraviolet light source connected to a light-transmitting pipe. The light transmitting pipe passes through the conductive cathode, thereby transmitting ultraviolet light from the pulsed ultraviolet light source into the impurity detection chamber and onto a photocathode on the surface of the conductive cathode end of the light-transmitting pipe. It is preferred that the photocathode be in electrical contact with the conductive cathode.

BRIEF DESCRIPTION OF THE DRAWINGS

The invention can be best understood by those having ordinary skill in the art by reference to the following detailed description when considered in conjunction with the accompanying drawings in which:

FIG. 4 illustrates a sequence of cross-sectional views showing the operation of the present invention.

DETAILED DESCRIPTION OF THE INVENTION

Figure 1:
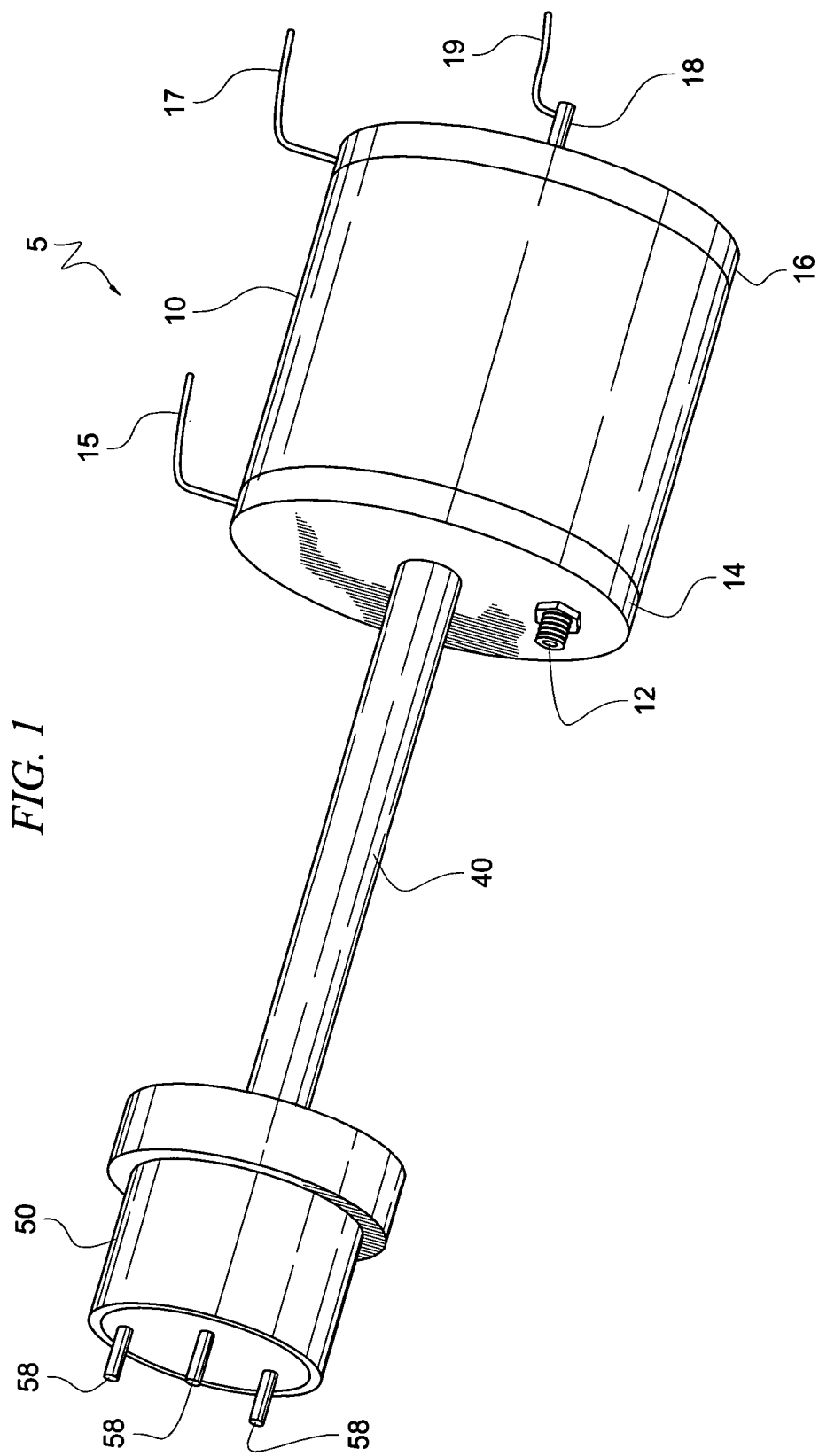
FIG. 1 illustrates an isometric view of the present invention.

Reference will now be made in detail to the presently preferred embodiments of the invention, examples of which are illustrated in the accompanying drawings. Throughout the following detailed description, the same reference numerals refer to the same elements in all figures.

Referring to FIG. 1, an isometric view of the present invention is shown. The impurity detector consists of an impurity detection chamber 5 and a pulsed ultraviolet light source 50, coupled together by a light-transmitting pipe 40 (an example of such a pulsed ultraviolet light source is a Perkin Elmer xenon flashlamp, part #FX-1152, an example of a light transmitting pipe is a quartz light-transmitting rod, Herasil 102, 361 mm long rod). It is preferred that the wavelength of the ultraviolet light is less than 240 nm (<2400 Angstroms). Although it is preferred to use a quarts rod for the light transmitting pipe 40. Other forms of light transmitting pipes are possible including a tube coated with aluminum on the inside, the aluminum coated with magnesium fluoride, thereby sealing the aluminum to prevent oxidation. The pipe must efficiently conduct ultraviolet light and any oxidation absorbs UV, reducing the efficiency of the light pipe.

The impurity detection chamber 5 has a hollow body 10. In the preferred embodiment, the impurity detection chamber 5 is cylindrical in shape and is made from a sturdy, resistive material, preferably doped ceramic. A material such as doped ceramic does not oxidize or produce impurities and, being doped, conducts electricity, thereby forming a resistor creating a relatively linear voltage drop across the hollow body when voltage is applied. In another embodiment, the hollow body is cylindrical in shape and is made from a plurality of alternating insulative layers and conductive layers. Preferably, the insulative layers are made from ceramic and the conductive layers from stainless steel. In some embodiments, the hollow body 10 and conductive ends 14/16 are designed to contain the liquid noble gas while in other embodiments, the hollow body 10 and conductive ends 14/16 are designed to be immersed in a larger vessel (not shown) and the larger vessel contains the liquid noble gas. In the later embodiment, openings 12 in one or both of the conductive ends 14/16 allow the noble gas to move freely to and from the vessel in which the impurity detection chamber 5 is submerged and into and out of the impurity detection chamber 5.

The ends of the hollow body 10 are capped with conductive ends 14/16. In the preferred embodiment, the conductive ends are made from stainless steel. Other conductive materials can be used, but oxidation must be prevented. The light-transmitting pipe 40 passes through an opening in the conductive cathode end 14 allowing the ultraviolet into the impurity detection chamber 5. In one of the conductive ends 14/16, there is at least one fitting or opening 12 to permit evacuation of the chamber and introduction/removal of the liquid to be measured. In an alternate embodiment of the present invention, the fitting or opening 12 or several openings in the conductive ends 14/16 allow free movement of the liquid noble gas into and out of the hollow body 10. In this embodiment, the detection chamber 5 is submerged within a larger vessel (not shown) containing the liquid noble gas and the cited purification mechanism, thereby permitting repeated purification/detection cycles until the desired level of purity is achieved.

Wires 15/17 are connected to the conductive ends 14/16 for connecting to a source of high-voltage direct current, the conductive ground plate 16 connected to a ground potential and a negative high voltage connected to the conductive cathode 14. In the preferred embodiment, the high voltage is approximately 700 VDC. Since the hollow body 10 is resistive, the high-voltage is divided across the surface of the hollow body 10 creating a uniform electric field.

The ultraviolet light source 50 has connections 58 to provide power and a trigger signal to the ultraviolet light source. A sense lead 18 is connected to a wire 19 for sensing the levels of impurity.

Although not shown, in some embodiments, a means for purifying the gas is also present in the detection chamber 5 or in the vessel that contains the detection chamber 5. One known method to purify Xenon (Xe) of Oxygen ($O_2$) molecules is to initiate a spark between a titanium electrode and a stainless steel electrode that are immersed in the liquid Xenon (Xe) within the detection chamber or within the vessel holding the liquid Xenon (Xe). The spark creates titanium dust that readily oxidizes by mixing with any available electro-negative molecule such as Oxygen ($O_2$) molecules. Methods such as this are known to iteratively produce Xenon (Xe) gas with purity levels at or below 1 ppb, and the impurity detection chamber of the present invention quickly and accurately measures the resulting impurity levels.

Figure 2:
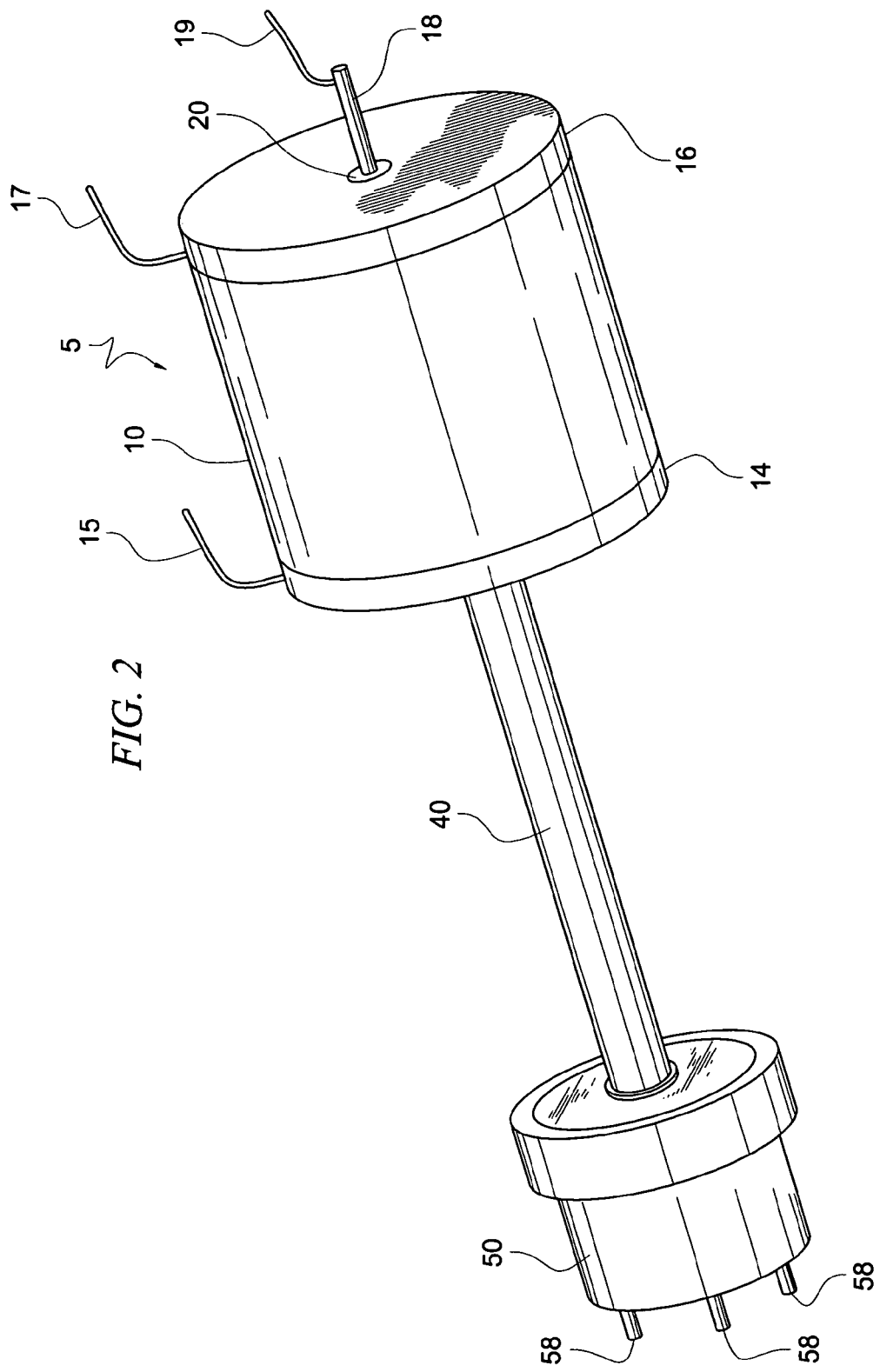
FIG. 2 illustrates a second isometric view of the present invention.

Referring to FIG. 2, a second isometric view of the present invention is shown. The impurity detector consists of an impurity detection chamber 5 and a pulsed ultraviolet light source 50, coupled together by a light-transmitting pipe 40. The impurity detection chamber 5 has a hollow body 10 that is, in the preferred embodiment, cylindrical in shape and made from a sturdy, resistive material, preferably doped ceramic. The ends of the hollow body 10 are capped with conductive ends 14/16. In the preferred embodiment, the conductive ends are made from stainless steel. Other conductive materials can be used, but oxidation must be prevented. Wires 15/17 are connected to the conductive ends 14/16 for connecting to a source of high-voltage direct current. Since the hollow body 10 is resistive, a high-voltage applied to the conductive cathode 14 and conductive ground plate 16 is divided across the surface of the hollow body 10.

The ultraviolet light source 50 has connections 58 to provide power and a trigger signal to the ultraviolet light source. A sense lead 18 is connected to a wire 19 for sensing the levels of impurity and is insulated from the conductive end 16 by an insulator 20.

Figure 3:
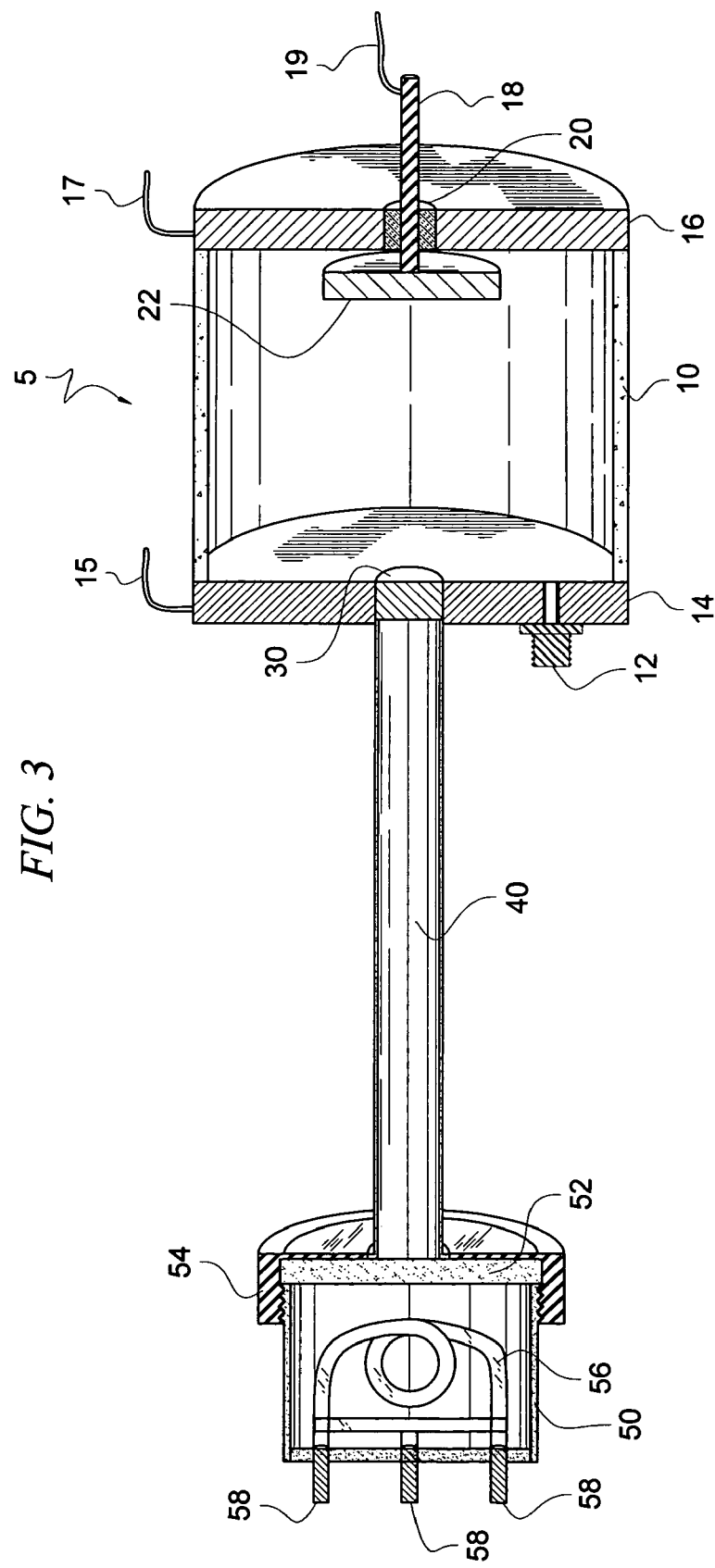
FIG. 3 illustrates a cross-sectional view of the present invention.

Referring to FIG. 3, a cross-sectional view of the present invention is shown. The impurity detector consists of an impurity detection chamber 5 and a pulsed ultraviolet light source 50, coupled together by a light-transmitting pipe 40. The pulsed ultraviolet light source 50 includes a flash tube 56 with electrical connections 58. In some embodiments, a sapphire window 52 allows the ultraviolet light emitted from the flash tube 56 to enter the detection chamber 5 and is held in place by a cover 54. Light from the flash tube 56 passes through the sapphire window 52 and through the light-transmitting pipe 40 until it reaches a photo cathode 30 at the end of the light-transmitting pipe 40, where it emits electrons into the detection chamber 5. In the preferred embodiment, the photo cathode 30 is made from gold and is approximately 13 nm to 15 nm thick, equal to one mean free path for light having a wavelength of 243 nm, which corresponds to gold's work function value of 5.1 eV. It is also preferred that the gold is in electrical contact with the conductive cathode 14.

In the preferred embodiment, the detection chamber 5 has a hollow body 10 that is cylindrical in shape and is made from a sturdy, resistive material such as doped ceramic. The ends of the hollow body 10 are capped with conductive ends 14/16. In the preferred embodiment, the conductive ends are made from stainless steel. Other conductive materials can be used, but oxidation must be prevented. Wires 15/17 are connected to the conductive ends 14/16 for connecting to a source of high-voltage direct current. Since the hollow body 10 is resistive, the high-voltage applied to the conductive cathode 14 and the conductive ground plate 16 is divided evenly across the surface of the hollow body 10. A sense anode 22 is connected to the sense lead 18, which is connected to a wire 19 for sensing the levels of impurity. The sense lead 18 is insulated from the conductive end 16 by an insulator 20. There is at least one fitting or opening 12 for inserting and removing the noble gas into and from the impurity detection chamber 5. In an alternate embodiment of the present invention, the fitting 12 or one-or more openings in the conductive ends 14/16 allows free movement of the liquid noble gas into and out of the hollow body 10. In this embodiment, the detection chamber 5 is submerged within a larger vessel (not shown) containing the liquid noble gas and the cited purification mechanism is also in the larger vessel, thereby permitting repeated purification/detection cycles until the desired level of purity is achieved.

After the light pulse introduces electrons into the impurity detection chamber 5, a cloud of electrons is created. The cloud of electrons drift towards the sensing anode 22 because of the effect of the stepped voltage drop on the walls of the hollow body 10 and the positive voltage charge on the ground plate 16. If there are impurities within the detection chamber 5, the electrons will bond with any impurity atom they encounter and never reach the sensing anode 22. If there are a large number of impurity molecules, few or no electrons will reach the anode 22, producing little or no output signal. If there are no impurities, most all of the electrons will reach the anode 22, yielding a much stronger output signal. Generally, the output signal is amplified by a high gain amplifier (not shown) and displayed on an oscilloscope or analyzed to convert the signal into a metered parts-per-billion value.

Referring to FIG. 4a through FIG. 4d, a sequence of cross-sectional views showing the operation of the present invention is shown. In FIG. 4a through FIG. 4d, exemplary numbers of electrons and impurity molecules are greatly reduced for the purpose of illustration while in reality, thousands of electrons are emitted and a varying number of impurity molecules are be present.

In FIG. 4a-FIG. 4d, the impurity detection chamber 5 and pulsed light source 50 are coupled by a light-transmitting pipe 40 and the impurity detection chamber 5 has a conductive cathode 14 connected to a negative high voltage and a conductive ground plate 16 connected to ground potential. The sensing anode 22 is connected to a sense lead 18 and the sense lead 18 is connected to an amplifier 60 through a wire 19. The output signal from the amplifier 60 is shown pictorially on oscilloscope screens 70/72/74/76.

In FIG. 4a, it can be seen that there are impurities within the liquid noble gas within the impurity detection chamber 5 as indicated by three oxygen molecules ($O_2$). No pulse of light has been emitted from the pulsed light source 50 and no signal is present on the oscilloscope 70.

In FIG. 4b, a pulse of light 62 has been emitted from the pulsed light source 50 and it has traveled down the light-transmitting pipe 40 and has struck the photo cathode 30 of the quartz rod, thereby knocking off electrons from the photocathode, creating an electron cloud as depicted by five e symbols within the impurity detection chamber 5. There are impurities within the liquid noble gas within the impurity detection chamber 5 as depicted by three oxygen ($O_2$) molecules. At this stage, no electrons have yet floated to the sensing anode 22, so there is still no signal present on the oscilloscope 72. Note that using five electrons and three oxygen molecules is for the purpose of this illustration and in reality, thousands of electrons are emitted and a varying number of impurity molecules may be present.

In FIG. 4c, it can be seen that three of the five electrons have bonded with the three oxygen ($O_2$/e) molecules. Two of the electrons didn't bond with any oxygen molecules and are attracted to the sensing anode 22 by the relatively positive voltage at the conductive ground plate 16, thereby reaching the sensing anode 22 and creating a small pulse on the oscilloscope 74. The greater the amount of impurities, fewer electrons will reach the sensing anode 22, and hence the signal will vary inversely to the level of impurities. Therefore, fewer impurities results in a greater number of electrons reaching the sensing anode 22, and hence generating a larger output pulse.

In FIG. 4d, there is only one oxygen molecule ($O_2$) in the impurity detection chamber 5, and the oxygen molecule ($O_2$) bonded with only one electron out of the five electrons shown, allowing four electrons to reach the sensing anode 22, thereby generating a higher pulse on the oscilloscope 76.

Figure 5:
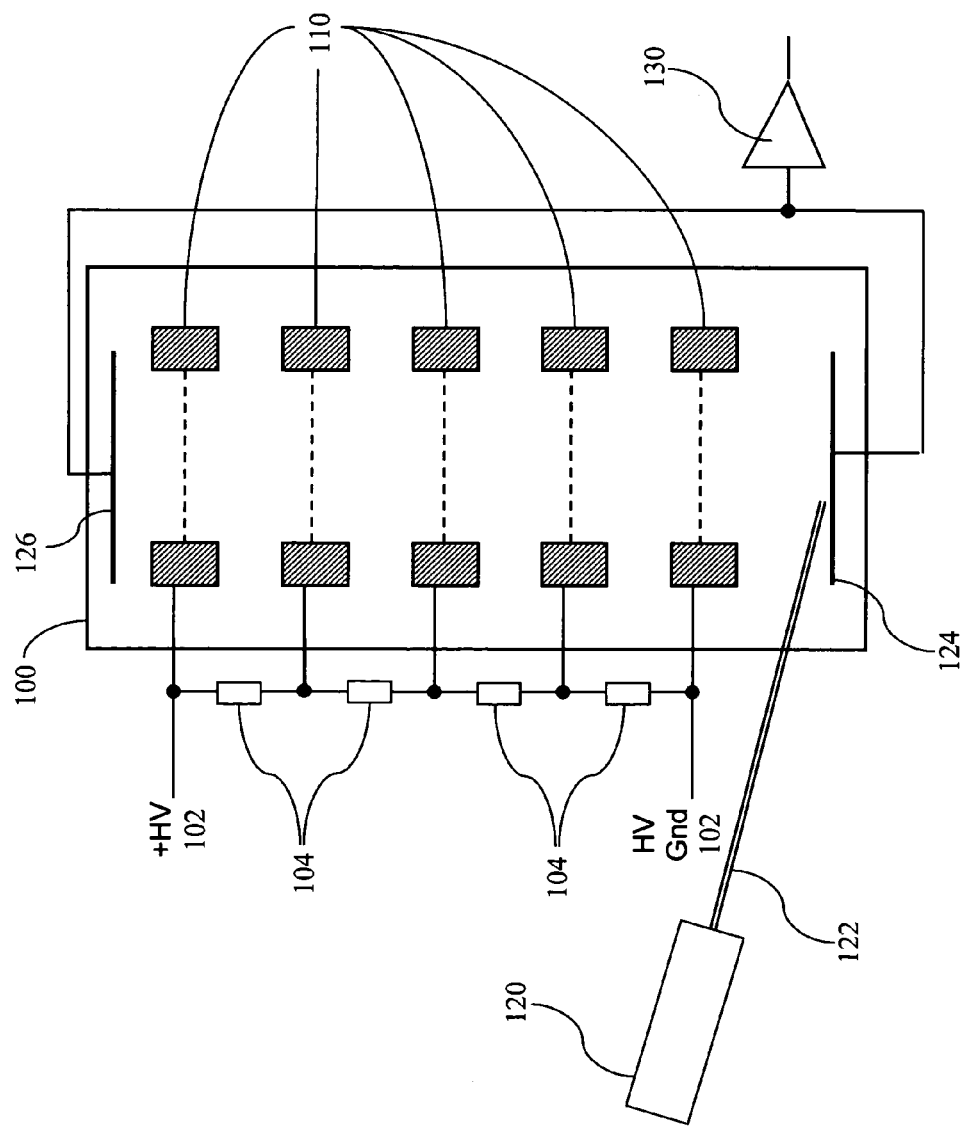
FIG. 5 illustrates an impurity detector of the prior art.

Referring to FIG. 5, an impurity detector of the prior art is shown. This impurity detector is described in a publication titled, "Argon Purification in the liquid phase," published in the Nuclear Instruments and Methods in Physics Research A 333 (1993), p567-570, North Holland. As shown in FIG. 5 (and in the reference), a purity monitor chamber 100 is filled with a noble gas of which the impurity level is to be measured. A high voltage 102 is placed over a resistor divider network 104 creating voltage steps that are coupled to a series of grid elements 110. A laser 120 is pulsed to emit a light beam through a fiber optic 122 and hits the photocathode 124 creating a pulse output that is sensed by an amplifier 130. Electrons flowing from the photocathode 124 drift towards the anode 126 and are again sensed by the amplifier 130. If there are no impurities in the noble gas, the amplitude of the anode pulse is equivalent to the amplitude of the cathode pulse. In contrast, if impurities exist, the amplitude of the anode pulse is lower than the amplitude of the cathode pulse in proportion to the amount of impurities.

Figure 6:
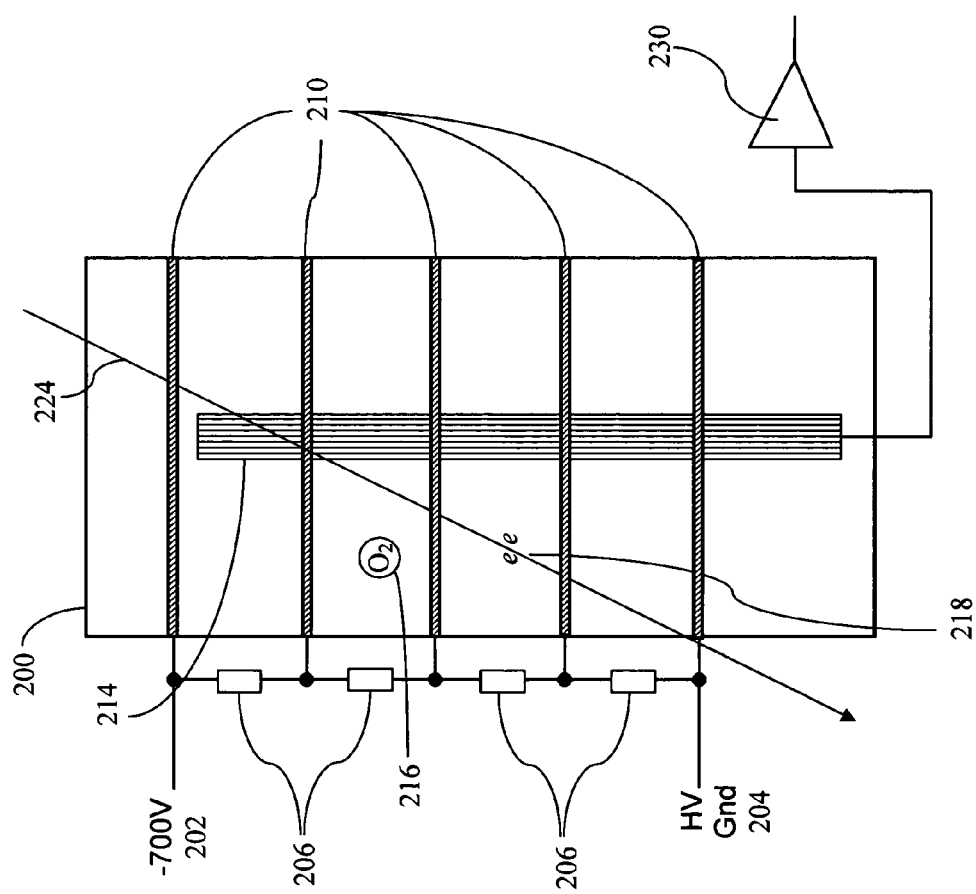
FIG. 6 illustrates another impurity detector of the prior art.

Referring to FIG. 6, illustrates another impurity detector of the prior art is shown. A purity monitor chamber 200 is made from an insulative material such as ceramic and has a plurality of conductive bands 210 insulated from each other by the insulative material. The conductive bands 210 are usually made from stainless steel. The chamber 200 is filled with a noble gas of which the impurity level is to be measured, for example liquid Xenon (Xe). A high voltage 202, perhaps 700 VDC, is placed over a resistor divider network 216 creating voltage steps that are coupled to the series of conductive bands 210. Within the tank is a stainless steel anode 214 connected to a high-gain amplifier 230. In our atmosphere, we are constantly bombarded with cosmic ray particles. As each cosmic ray particle hits the Earth's atmosphere, a nuclear reaction occurs which produces pions that decay into muons. When a muon passes through the Xenon gas 224, it produces an ionized track 224. The negative electrons 218 and the positive ions separate in the electric field, with the electrons drifting towards the anode 214 and the ions drifting towards the cathode 202. If impurity molecules are present such as an oxygen molecule 216, some of the electrons bond with the impurity molecule and never reach the anode 214. The electrons that do reach the anode 214 are amplified by the high-gain amplifier 230 and, thereby, are detected. If the Xenon (Xe) gas was 100% pure, all of the electrons from the ionization would reach the anode 214 and be detected. The average magnitude of the detected signal is measured to determine the estimated purity of the Xenon (Xe). Unfortunately, to achieve a useful measurement, many muons must pass through the Xenon (Xe) gas, requiring approximately one half of an hour to make a reliable measurement.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for detecting impurities within a noble gas, the device comprising:
   an impurity detection chamber for holding the noble gas in liquid form, the impurity detection chamber comprising:
      a body having a first open end and a distal second open end, the body is hollow;
      a conductive cathode interfaced at the first open end of the body;
      a conductive ground plate interfaced at the distal second open end of the body;
      a conductive sensing anode within the impurity detection chamber in proximity to and insulated from the conductive ground plate, the conductive sensing anode connected to a conductive sensing lead which is insulated from and passes through the conductive ground plate;
      a pulsed ultraviolet light source; and
      a light-transmitting pipe having a first end and a second end, the first end of the light transmitting pipe interfaced to the pulsed ultraviolet light source, the second end of the light transmitting pipe passing through the conductive cathode, thereby transmitting ultraviolet light from the pulsed ultraviolet light source into the impurity detection chamber and onto a photocathode situated on the surface of the second end of the light-transmitting pipe.

2. The device of claim 1, wherein the photocathode is a thin layer of gold.

3. The device of claim 2, wherein the thin layer of gold is approximately 13 to 15 nanometers (nm) thick.

4. The device of claim 1, wherein the photocathode is in electrical contact with the conductive cathode.

5. The device of claim 1, wherein the body is cylindrical in shape.

6. The device of claim 1, wherein the body is made from doped ceramic and is partially conductive.

7. The device of claim 1, wherein the conductive cathode, the conductive ground plate and the conductive sensing anode are made from stainless steel.

8. The device of claim 1, further comprising a fitting passing through the conductive cathode for evacuating the impurity detection chamber and for introducing and extracting the noble gas into and out of the impurity detection chamber.

9. The device of claim 1, wherein the light transmitting pipe is a quartz rod.

10. The device of claim 1, further comprising a sapphire window adapted between the pulsed ultraviolet light source and the light transmitting pipe.

11. The device of claim 1, wherein the pulsed ultraviolet light source is a xenon flash tube.

12. The device of claim 1, wherein a high negative voltage is applied to the conductive cathode with respect to a ground potential at the conductive ground plate.

13. The device of claim 12, wherein the high negative voltage is approximately minus 700 volts direct current.

14. A method for detecting impurities within a noble gas, the method comprising:
providing an impurity detection chamber for holding the noble gas in liquid form, the impurity detection chamber comprising:
a body having a first open end and a distal second open end, the body is hollow;
a conductive cathode affixed to the first end of the body, the conductive cathode connected to a negative source of electricity;
a conductive ground plate affixed to the distal second open end of the body, the conductive ground plate connected to an electrical ground;
a conductive sensing anode within the impurity detection chamber in proximity to and insulated from the conductive ground plate, the conductive sensing anode connected to a conductive sensing lead which is insulated from and passes through the conductive ground plate;
evacuating the impurity detection chamber;
filling the impurity detection chamber with the noble gas in liquid form;
emitting a pulse of ultraviolet light from a source of pulsed ultraviolet light;
conducting the pulse of ultraviolet light into the impurity detection chamber and onto a photocathode, thereby creating a cloud of electrons;
attracting the cloud of electrons toward the conductive sensing anode by way of a relatively positive voltage potential-at the conductive ground plate with respect to the conductive cathode; and
measuring a voltage potential created by a number of electrons from the cloud of electrons that reach the conductive sensing anode, whereby the number of electrons reaching the conductive sensing anode relates inversely with an amount of impurities within the noble gas.

15. The method of claim 14, wherein the photocathode is a thin layer of gold.

16. The method of claim 15, wherein the thin layer of gold is approximately 13 to 15 nanometers (nm) thick.

17. The method of claim 14, wherein the photocathode is in electrical contact with the conductive cathode.

18. The method of claim 14, wherein the body is cylindrical in shape.

19. The method of claim 14, wherein the body is made from doped ceramic and is partially conductive.

20. The method of claim 19, wherein a voltage difference between the conductive cathode and the conductive ground plate is distributed over the partially conductive body, thereby improving the movement of the electron cloud towards the conductive sensing anode.

21. The method of claim 14, wherein the conductive cathode, the conductive ground plate and the conductive sensing-anode are made from stainless steel.

22. The method of claim 14, further comprising a fitting passing through the conductive cathode for evacuating the impurity detection chamber and for introducing the noble gas into the impurity detection chamber.

23. The method of claim 14, wherein the light transmitting pipe is a quartz rod.

24. The method of claim 14, further comprising a sapphire window adapted between the pulsed ultraviolet light source and the light transmitting pipe.

25. The method of claim 14, wherein the negative source of electricity connected to the conductive cathode is approximately −700 volts direct current with respect to the conductive ground plate.

26. A device for detecting impurities within a noble gas, the device comprising:
an impurity detection chamber for holding the noble gas in liquid form, the impurity detection chamber comprising:
a body having a first open end and a distal second open end, the body is hollow and comprises a plurality of conductive elements insulated from each other;
a conductive cathode affixed at the first end of the body;
a conductive ground plate affixed at the distal second end of the body;
a conductive sensing anode within the impurity detection chamber in proximity to and insulated from the conductive ground plate, the conductive sensing anode connected to a conductive sensing lead which is insulated from and passes through the conductive ground plate;
a high voltage source of direct current whereby a negative potential of the direct current is applied to the conductive cathode and a ground potential of the direct current is applied to the conductive ground plate and the high voltage source is divided into substantially equal-stepped potentials, each of the substantially equal-stepped potentials is connected, in order, to the plurality of conductive elements;
a pulsed ultraviolet light source; and
a light-transmitting pipe having a first end and a second end, the first end of the light transmitting pipe interfaced to the pulsed ultraviolet light source, the second end of the light transmitting pipe passing through the conductive cathode, thereby transmitting ultraviolet light from the pulsed ultraviolet light source into the impurity detection chamber and onto a photocathode, the photocathode situated on the surface of the second end of the light-transmitting pipe.

27. The device of claim 26, wherein the photocathode is a thin layer of gold.

28. The device of claim 27, wherein the thin layer of gold is approximately 13 to 15 nanometers (nm) thick.

29. The device of claim 26, wherein the photocathode is in electrical contact with the conductive cathode.

30. The device of claim 26, wherein the body is cylindrical in shape.

31. The device of claim 26, wherein the conductive cathode, the conductive ground plate, the plurality of conductive elements and the conductive sensing anode are made from stainless steel.

32. The device of claim 26, wherein the plurality of conductive elements are insulated from each other by ceramic spacers.

33. The device of claim 26, further comprising a fitting passing through the conductive cathode for evacuating the impurity detection chamber and for introducing and extracting the noble gas into and out of the impurity detection chamber.

34. The device of claim 26, wherein the light transmitting pipe is a quartz rod.

35. The device of claim 26, further comprising a sapphire window adapted between the pulsed ultraviolet light source and the light transmitting pipe.

36. The device of claim 26, wherein the pulsed ultraviolet light source is a xenon flash tube.

37. The device of claim 26, wherein the high voltage source of direct current is approximately 700 volts.

* * * * *